United States Patent
Hotta

(10) Patent No.: US 7,608,232 B2
(45) Date of Patent: Oct. 27, 2009

(54) TREATMENT METHOD AND TREATMENT APPARATUS FOR GAS CONTAINING NITROUS OXIDE

(75) Inventor: Masatoshi Hotta, Kawasaki (JP)

(73) Assignee: Showa Denko K.K., Tokyo (JP)

( * ) Notice: Subject to any disclaimer, the term of this patent is extended or adjusted under 35 U.S.C. 154(b) by 182 days.

(21) Appl. No.: 11/791,343

(22) PCT Filed: Nov. 15, 2005

(86) PCT No.: PCT/JP2005/021313

§ 371 (c)(1),
(2), (4) Date: May 23, 2007

(87) PCT Pub. No.: WO2006/059506

PCT Pub. Date: Jun. 8, 2006

(65) Prior Publication Data

US 2007/0292334 A1 Dec. 20, 2007

Related U.S. Application Data

(60) Provisional application No. 60/633,423, filed on Dec. 7, 2004.

(30) Foreign Application Priority Data

Nov. 30, 2004 (JP) ............................. 2004-345669

(51) Int. Cl.
*B01D 53/56* (2006.01)
*B01J 15/00* (2006.01)

(52) U.S. Cl. ................. 423/239.1; 422/105; 422/168; 422/173; 422/177

(58) Field of Classification Search ............ 423/239.1; 165/186; 422/105, 168, 173, 177
See application file for complete search history.

(56) References Cited

U.S. PATENT DOCUMENTS

| 4,259,303 A * | 3/1981 | Nakaji et al. ............. 423/239.1 |
| 4,877,743 A * | 10/1989 | Waugh et al. ............... 436/116 |
| 2003/0185735 A1* | 10/2003 | Hotta et al. .............. 423/239.1 |
| 2004/0109804 A1* | 6/2004 | Van den Brink et al. . 423/239.1 |
| 2005/0281724 A1* | 12/2005 | Hotta et al. .............. 423/239.1 |

FOREIGN PATENT DOCUMENTS

| DE | 820 894 C | 11/1951 |
| WO | WO 02/26355 A2 | 4/2002 |
| WO | WO 03/080230 A1 | 10/2003 |

* cited by examiner

*Primary Examiner*—Timothy C Vanoy
(74) *Attorney, Agent, or Firm*—Sughrue Mion, PLLC

(57) ABSTRACT

Nitrous oxide-containing gas is subjected to heat exchange with decomposed gas from a nitrous oxide decomposition catalyst-filled reactor and then contacted with a heater comprising integrally formed heating unit and baffles, wherein gaps are formed between the baffle-integrated heater and the unit body in order to alleviate the pressure difference in the gas flow channel, and subsequently introduced into a nitrous oxide catalyst-filled catalyst layer for decomposition of the nitrous oxide into nitrogen and oxygen. The nitrous oxide-containing gas is neutralized by continuous treatment.

10 Claims, 2 Drawing Sheets

TREATMENT METHOD AND TREATMENT APPARATUS FOR GAS CONTAINING NITROUS OXIDE

CROSS-REFERENCE TO RELATED APPLICATION

This application is the National Stage of PCT/JP2005/021313 filed Nov. 15, 2005, and claims benefit of U.S. Provisional Application No. 60/633,423 filed Dec. 7, 2004.

TECHNICAL FIELD

The present invention relates to a treatment method and treatment apparatus for gas containing nitrous oxide

BACKGROUND ART

Anesthetic gas pollution in operating rooms and the health problems of operating room employees have been issues dealt with since 1960, and it is known that health can be impaired by long-term inhalation of anesthetic gas leaking into operating rooms. Anesthetic gas is mixed gas containing nitrous oxide, a volatile anesthetic agent and oxygen, while waste anesthetic gas is the anesthetic gas after respiration by the patient. The composition of waste anesthetic gas is similar to the composition of anesthetic gas, comprising a volatile anesthetic agent, high-concentration nitrous oxide and oxygen. In the United States, the National Institute for Occupational Safety and Health (NIOSH) recommends an environmental exposure level for nitrous oxide ($N_2O$) of no greater than 25 ppm, and for volatile anesthetic agents alone of 2 ppm or no greater than 0.5 ppm in combination with nitrous oxide. It has therefore become mandatory to equip all anesthesia machines with waste anesthetic gas scavenging units, currently allowing operating room environments to meet the aforementioned recommendation.

Nitrous oxide is also used throughout the world for painless childbirth and dental treatment, because of its analgesic and anesthetic effects. Since volatile anesthetic agents are not used for these purposes, the major components of waste anesthetic gas are nitrous oxide, oxygen and carbon dioxide. Likewise, it has become possible for environments in delivery rooms to meet the aforementioned recommendations.

Waste anesthetic gas scavenging units are devices which combine compressed air or the like with waste anesthetic gas from patient exhalation, or eliminate it using a vacuum pump or the like. However, the gas removed from operating rooms, delivery rooms or dental clinics using such waste anesthetic gas scavenging units is currently ejected into the atmosphere without protective measures.

With recent focus on the problem of global warming, the Conference of Parties III (COP3) for Prevention of Global Warming has particularly specified nitrous oxide, together with nitrogen dioxide, methane, freon gas and the like, as a global environmental pollutant which increases global temperatures through a greenhouse effect (a warming effect of approximately 300 times that of carbon dioxide).

In addition, nitrous oxide is also being increasingly used for semiconductor manufacturing processes, heightening the need for measures toward protection of the global environment.

From the viewpoint of global environmental protection, it has become essential to remove or neutralize volatile anesthetic agents and nitrous oxide in waste anesthetic gas when using waste anesthetic gas scavenging units for discharge of waste anesthetic gas, instead of simply discharging it into the air.

Normally, the waste gas discharged from a single operating room, at most medical facilities, is 30-40 L/min including the indoor air accompanying it. However, a variety of waste anesthetic gas scavenging units and discharge methods are used at different medical facilities, and some of these far exceed the treatment capacity of conventional waste anesthetic gas treatment apparatuses. For example, with a discharge line for an entire operating room, including ventilation gas, the treatment volume is 1 $m^3$/min or greater, and the reactor used for treatment at such a flow rate is usually of a type for a small plant. Thus, an increased flow rate requires a large waste anesthetic gas treatment apparatus, resulting in a larger heat exchanger for heating of the large volume of treatment gas to the prescribed temperature and a larger size and volume of its heater, and problems of increased energy consumption and installation space and weight restrictions may arise when the treatment apparatus is installed in a hospital. Particularly when using a system of adsorption removal of volatile anesthetic agents, a large flow of treatment gas results in more rapid breakthrough of the adsorbent, necessitating a much larger unit for implementation and making it difficult to achieve actual practical use.

On the other hand, waste anesthetic gas discharged from delivery rooms and dental treatment clinics consists of nitrous oxide and oxygen, without volatile anesthetic agents, and therefore the units used for its treatment are less complex; however, because of the problems mentioned above, it has not yet been possible to implement units which continuously and efficiently treat the nitrous oxide contained in the waste anesthetic gas at a flow rate of 1 $m^3$/min or greater. For continuous and efficient treatment of nitrous oxide contained in large-volume waste anesthetic gas it is not sufficient merely to increase the size of the treatment apparatus, and limitations also exist on the size of the installation space and on the weight, such that modification of parts are necessary in order to increase energy efficiency and reduce space requirements. Yet such treatment methods and treatment apparatuses are as yet unknown, and therefore in light of the growing awareness of the contribution of nitrous oxide to global warming, a demand exists for development of a treatment method and treatment apparatus capable of continuously treating nitrous oxide-containing gas that is discharged, particularly at large circulation rates, from operating rooms, delivery rooms and dental clinics.

Examples of conventional treatment apparatuses include (1) the high-temperature catalyst unit described in Japanese Unexamined Patent Publication No. 64-511126, (2) the integrated heat exchanger and catalyst reactor described in Japanese Unexamined Patent Publication No. 2004-920, and (3) the contact oxidation unit described in Japanese Unexamined Patent Publication No. 55-56823. The high-temperature catalyst unit proposed in (1) is a reactor having a heat exchanger and a catalyst-filled section in an integrated structure, but because the reactor is built to small specifications, a large circulation flow can result in insufficient heat efficiency of heat transfer at the heater. Also, in the example of an ordinary reactor described in (FIG. 5 of) (1) above, the heater lacks baffles and therefore the heater fails to efficiently utilize heat regardless of the flow rate.

Moreover, in the integrated heat exchanger/catalyst reactor of (2) above, despite the structure of the reactor wherein the heat exchanger and reactor are integrated, the structural characteristics of the reactor allow it to exhibit sufficient treatment capacity for treatment flow rates of up to 1 $m^3$/min, but pressure loss increases with greater flow rates, such that intended flow cannot be achieved in the reactor and adequate treatment cannot be accomplished.

With the contact oxidation unit of (3) above, the heat exchanger and heater are fixed, and therefore any trouble with the heater requires exchange of both the heat exchanger and heater sections, causing a problem in terms of maintenance and cost.

Methods of catalytic decomposition are described, for example, in (4) Japanese Examined Patent Publication No. 61-45486 and Japanese Examined Patent Publication No. 62-27844, wherein nitrous oxide is decomposed with a catalyst. Although these methods can decompose high concentrations of nitrous oxide, the nitrogen oxides nitrogen monoxide (NO) and nitrogen dioxide ($NO_2$) (hereinafter referred to as $NO_x$) are produced at 5-32 ppm, in some cases leading to the problem of $NO_x$ production exceeding 3 ppm as the permissible concentration for $NO_2$ (TWA: time-weighted average). In addition, the method proposed in (4) above requires a contact time of 0.2 second or longer, i.e. a space velocity (SV) of no greater than 18,000 $Hr^{-1}$, and therefore the treatment volume is limited. A larger SV shortens the contact time, resulting in problems such as reduced reaction efficiency.

DISCLOSURE OF INVENTION

It is an object of the present invention to provide a method and unit for treatment of gas containing nitrous oxide.

As a result of much diligent research directed toward achieving the aforementioned object, the present inventors have discovered that nitrous oxide can be efficiently decomposed into oxygen and nitrogen to solve the problems described above, if nitrous oxide-containing gas discharged from, for example, delivery rooms and dental clinics or from semiconductor manufacturing processes is introduced into a flow channel comprising a heating unit and multiple gaps, the gas is split into a gas stream flowing along the flow channel and a gas stream flowing through the gaps formed in the flow channel, the gas stream flowing along the flow channel is directed to merge with the split gas stream, and the gas is contacted with the heating unit to raise the temperature to a prescribed temperature before contacting with a catalyst; the present invention was thereupon completed.

More specifically, nitrous oxide-containing gas is heat exchanged with exiting gas which has undergone nitrous oxide decomposition treatment, and then contacted with a heating unit integrally formed with baffles to raise the temperature to a prescribed temperature prior to contact with the nitrous oxide decomposing catalyst.

According to the invention, the use of a heating unit integrally formed with baffles permits the heating unit to be easily detached from the apparatus for more efficient maintenance and replacement of the heater exchanger and heater. Also, by providing gaps between the baffles on the wall of the heating unit integrally formed with the baffles, or by providing gaps between the baffles of the heating unit and the baffles formed on the walls of the decomposition reaction unit, it is possible to alleviate pressure during gas circulation and reduce the pressure loss with circulation at a flow rate of 1 $m^3$/min or greater. Furthermore, since the baffles and heater have an integral structure, they can be detached from the heat exchanger during periods of trouble or maintenance, so that the heater alone may be exchanged instead of the entire heat exchanger, thereby providing a major advantage in terms of handleability and cost.

Thus, the present invention relates to the following [1] to [10].

[1] A treatment method for nitrous oxide-containing gas, wherein in a method of contacting nitrous oxide-containing gas with a catalyst for decomposition treatment of the nitrous oxide in the gas, the gas is introduced into a flow channel comprising a heating unit and multiple gaps, the gas is split into a gas stream flowing along the flow channel and a gas stream flowing through the gaps formed in the flow channel, the gas stream flowing along the flow channel is directed to merge with the split gas stream, and the gas is contacted with the heating unit to raise the temperature to a prescribed temperature before contacting with a catalyst for decomposition of the nitrous oxide.

[2] A gas treatment method according to [1] above, wherein the gaps formed in the flow channel are either formed between the baffles integrally formed with the heating unit, or between the baffles integrally formed with the heating unit and the baffles formed on the walls of the decomposition reaction unit.

[3] A gas treatment method according to [1] or [2] above, wherein the concentration of the nitrous oxide contained in the gas is between 10 ppm and 30%.

[4] A gas treatment method according to any one of [1] to [3] above, wherein the nitrous oxide decomposition temperature is 200-600° C.

[5] A gas treatment method according to any one of [1] to [4] above, wherein the content of $NO_x$ produced during decomposition of the nitrous oxide is no greater than 5 ppm.

[6] A gas treatment method according to any one of [1] to [5] above, wherein the concentration of nitrous oxide contained in the nitrous oxide-decomposed gas is detected and the nitrous oxide decomposition temperature is controlled based on the detected nitrous oxide concentration.

[7] A treatment apparatus for nitrous oxide-containing gas, wherein a unit in which nitrous oxide-containing gas is contacted with a catalyst for decomposition treatment of the nitrous oxide in the gas comprises a heat exchanger, a heating unit integrally formed with baffles, a decomposition reactor filled with a nitrous oxide decomposition catalyst and a detector which detects the concentration of nitrous oxide in the gas exiting the decomposition reactor, wherein a gas flow channel is formed by the baffles integrally formed with the heating unit, the baffles formed on the walls of the decomposition reaction unit and the walls of the decomposition unit, while gaps are formed in the flow channel either between the baffles, or between the baffles and the baffles formed on the wall of the decomposition reaction unit.

[8] A gas treatment apparatus according to [7] above, wherein the nitrous oxide-containing gas is introduced into a heat exchanger and then allowed to flow through the gas flow channel and a decomposition reactor, and discharged after being again circulated through the heat exchanger.

[9] A gas treatment apparatus according to [7] or [8] above, which is provided with a temperature controlling unit which detects the concentration of nitrous oxide in the gas with the detector before and after it is introduced into the heat exchanger, and controls the temperature of the decomposition reactor based on the detected nitrous oxide concentration.

[10] A gas treatment apparatus according to any one of [7] to [9] above, wherein the heating unit integrally formed with the baffles is detachable from the decomposition treatment apparatus.

By using the gas treatment method and treatment apparatus of the invention, it is possible to efficiently heat nitrous oxide-containing gas discharged from delivery rooms, dental clinics and the like using a heat exchanger, and then decompose the nitrous oxide into nitrogen and oxygen. From the viewpoint of protecting the global environment, using the gas treatment method and treatment apparatus of the invention also can prevent release into the air of nitrous oxide, a gas which destroys the ozone layer and contributes to global warming, and render it harmless. The treatment apparatus of the invention is also compact despite its capacity for large volume treatment, and can therefore be installed on hospital roofs or inside hospital facilities with relatively limited space, such as in machine rooms or conduit spaces, while its ability to treat nitrous oxide-containing gas at greater than 1 m³/min in a continuous manner provides an economical advantage.

BEST MODE FOR CARRYING OUT THE INVENTION

Figure 1:
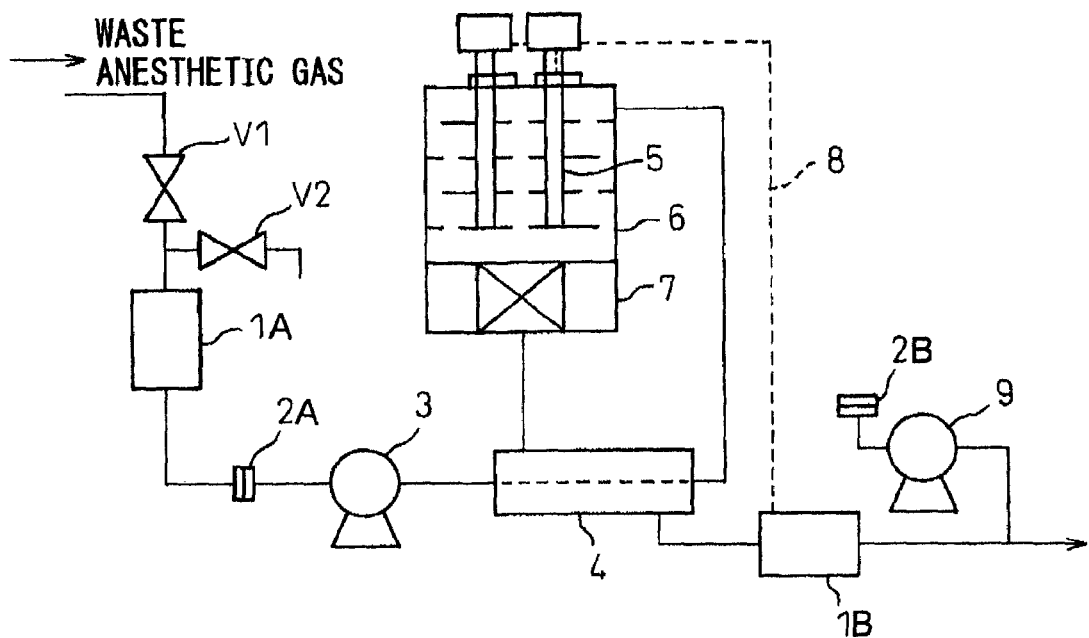
FIG. 1 is a schematic drawing showing an embodiment of a gas treatment apparatus according to the invention.

Preferred embodiments of the invention will now be explained in detail.

First, a method for treatment of nitrous oxide-containing gas according to the invention will be explained.

The gas treatment method of the invention is a method for treatment of gas wherein nitrous oxide-containing gas is introduced into a flow channel comprising a heating unit and multiple gaps, the gas is split into a gas stream flowing along the flow channel and a gas stream flowing through the gaps formed in the flow channel, the gas stream flowing along the flow channel is directed to merge with the split gas stream, and the gas is contacted with the heating unit to raise the temperature to a prescribed temperature before contacting with a catalyst for decomposition of the nitrous oxide.

According to the invention, the heater (heating unit) which heats the nitrous oxide-containing gas has a construction wherein the heater and baffles are integrated and circulation occurs through the heating unit provided with gaps between the heater and the body of baffles, thereby alleviating pressure differences within the flow channel, while it is sufficient to replace only the heater without having to replace the entire heat exchanger including the baffles during times of maintenance or heater trouble, so that operation is notably simplified compared to the prior art and a major advantage is provided in terms of handleability and cost.

Since interior air also enters the nitrous oxide decomposition unit when carrying out the method of the invention, dust in the interior air can contaminate the system. In order to prevent this, it is preferred to install a filter before the heat exchanger.

For example, nitrous oxide-containing gas discharged from a delivery room is discharged together with indoor ventilation air of the delivery room, and the nitrous oxide concentration is approximately 10-10,000 ppm. On the other hand, the nitrous oxide concentration of nitrous oxide-containing gas discharged from a dental clinic is 10-30%.

The nitrous oxide in the nitrous oxide-containing gas is then decomposed into nitrogen and oxygen using a nitrous oxide decomposition catalyst. The nitrous oxide decomposition catalyst is not particularly restricted and may be any existing catalyst such as, for example, an alumina-based catalyst with a precious metal supported on the alumina.

Decomposition of nitrous oxide can sometimes result in production of $NO_x$ exceeding permissible concentrations, and in order to limit the $NO_x$ production to no greater than 1 ppm, it is preferred to use at least one type of catalyst selected from the group consisting of the following (I) to (III) as the nitrous oxide decomposition catalyst.

(I) Catalysts having at least one type of metal selected from the group consisting of magnesium, zinc, iron and manganese, with aluminum and rhodium, carried on a support.

(II) Catalysts having at least one type of metal selected from the group consisting of magnesium, zinc, iron and manganese, with rhodium, carried on an alumina support.

(III) Catalysts having rhodium carried on a support formed of a spinel-type crystalline compound oxide with at least a portion of aluminum and at least one type of metal selected from the group consisting of magnesium, zinc, iron and manganese.

The temperature of the decomposition reactor filled with the nitrous oxide decomposition catalyst may be, for example, in the range of 200-600° C., preferably 300-500° C. and more preferably 350-450° C. Setting the temperature of the catalyst-filled decomposition reactor to within this temperature range will permit efficient decomposition of the nitrous oxide, while using the aforementioned decomposition catalyst will limit the $NO_x$ production to no greater than 1 ppm. If the temperature of the decomposition reactor is lower than 200° C., the nitrous oxide may not sufficiently decompose, while at a temperature of above 600° C. the life of the catalyst is shortened, and temperatures of above 600° C. are not desirable in terms of safety at facilities such as hospitals.

Generally, the concentration of nitrous oxide used in anesthetic gas is in a range of no greater than 70%. The waste anesthetic gas discharged from waste anesthetic gas scavenging units from delivery rooms is diluted to a nitrous oxide concentration of a few percent by the indoor air. A higher concentration of around 30% is found in dental clinics. While there is no problem in terms of the decomposing power of a catalyst if it is directly introduced into a catalyst layer, a lower concentration of nitrous oxide introduced into the catalyst layer is preferred from the viewpoint of catalyst activity and catalyst life. Thus, the gas introduced into the nitrous oxide decomposition reactor is diluted, preferably to a nitrous oxide concentration of no greater than 10% and more preferably no greater than 5%.

The gas used to dilute the nitrous oxide-containing gas is not particularly restricted so long as it is a gas which does not affect the catalyst, and for example, air, nitrogen or an inert gas such as helium or argon may be used. From the viewpoint of economy, dry air or direct atmospheric air is preferably used.

The temperature of the gas introduced into the nitrous oxide decomposition unit is approximately at ordinary temperature, but the gas decomposed by the catalyst is heated to 200-600° C. In the treatment method of the invention, therefore, the gases before and after introduction into the decomposition unit are circulated through the heat exchanger set at the exit port of the decomposition reactor for heat exchange between the gas being introduced into the decomposition unit and the gas being discharged from the decomposition unit, thereby allowing the heating energy and cooling energy to be reduced for increased energy efficiency. Increasing the energy efficiency in this manner allows the gas/catalyst contact time to be shortened to 0.2 second or less.

Also in the treatment method of the invention, the nitrous oxide concentration of the gas discharged from the decomposition unit is detected before it is released into the atmosphere, so that the reaction temperature of the decomposition unit can be controlled based on the detected concentration. The nitrous oxide concentration in the gas discharged from the exit port of the decomposition unit is monitored, allowing reduction in the activity of the nitrous oxide decomposition catalyst to be detected and allowing control, such as increase, of the decomposition reaction temperature based on the detected nitrous oxide concentration.

The treatment apparatus for nitrous oxide-containing gas according to the invention will now be explained.

The unit of the invention is a treatment apparatus for nitrous oxide-containing gas, wherein a unit in which nitrous oxide-containing gas is contacted with a catalyst for decomposition treatment of the nitrous oxide in the gas, comprises a heat exchanger, a heating unit integrally formed with a baffle, a decomposition reactor filled with a nitrous oxide decomposition catalyst and a detector which detects the concentration of nitrous oxide in the gas exiting the decomposition reactor, wherein a gas flow channel is formed by the baffles integrally formed with the heating unit, the baffles formed on the walls of the decomposition reaction unit and the walls of the decomposition unit, while gaps are formed in the flow channel either between the aforementioned baffles, or between the aforementioned baffles and the baffles formed on the wall of the decomposition reaction unit.

More specifically, it is characterized by comprising a heat exchanger for heat exchange between gas discharged from the nitrous oxide decomposition catalyst-filled reactor and untreated gas, and a heater having a structure with the heater heating unit integrated with baffles to facilitate replacement of the heater during maintenance, characterized in that the structure includes gaps between the aforementioned baffles, or between the aforementioned baffles and a baffles formed on the wall of the decomposition reactor, in order to alleviate the pressure difference produced in the flow channel, and in that it is provided with a decomposition reactor filled with the catalyst which decomposes the nitrous oxide in the gas and a detector which detects the nitrous oxide concentration in the gas before and after treatment.

The gaps between the aforementioned baffles, or between the aforementioned baffles and the baffles formed on the wall of the decomposition reactor, may be formed without any particular restrictions. However, the spacing is preferably not too wide because the gas to be treated will migrate before heat exchange, while conversely it is preferably not too narrow because the effect of reducing the pressure difference will be lessened and the operation for heater replacement will become inconvenient, and therefore the spacing between the gaps is preferably about 5-30 mm.

The heat exchanger for heat exchange between the gas discharged from the nitrous oxide decomposition catalyst-filled decomposition reactor and the untreated gas is connected to the decomposition reactor so that the nitrous oxide-containing gas which has passed through it is introduced into the nitrous oxide decomposition catalyst-filled decomposition reactor. Also, the heat-exchanged gas is heated while being introduced into the decomposition reactor, by a heater having a structure with an integrated heating unit and baffles.

The gas treatment apparatus of the invention will now be explained in greater detail with reference to the accompanying drawings.

FIG. 1 schematically shows an embodiment of a gas treatment apparatus of the invention wherein nitrous oxide-containing gas undergoes heat exchange before decomposition treatment and then the nitrous oxide is decomposed. The gas treatment apparatus shown in FIG. 1 comprises nitrous oxide detectors 1A and 1B. filters 2A and 2B, a blower 3 for aspiration of the nitrous oxide-containing gas, a heater exchanger 4, a baffle-integrated heater 5, a nitrous oxide decomposition reactor 6, a nitrous oxide decomposition catalyst 7, a reaction temperature control circuit 8, a reacted gas diluting blower 9, a treatment gas introduction valve V1 and a purge valve V2.

In the gas treatment apparatus of FIG. 1, the gas to be treated is introduced into the nitrous oxide detector 1A through the valve V1, and then introduced into the nitrous oxide decomposition reactor 6 through the filter 2A and heat exchanger 4. Indoor air is aspirated through the valve V2 until the temperature of the catalyst layer of the reactor 6 reaches a prescribed temperature, but the valve V2 is not essential.

Figure 2:
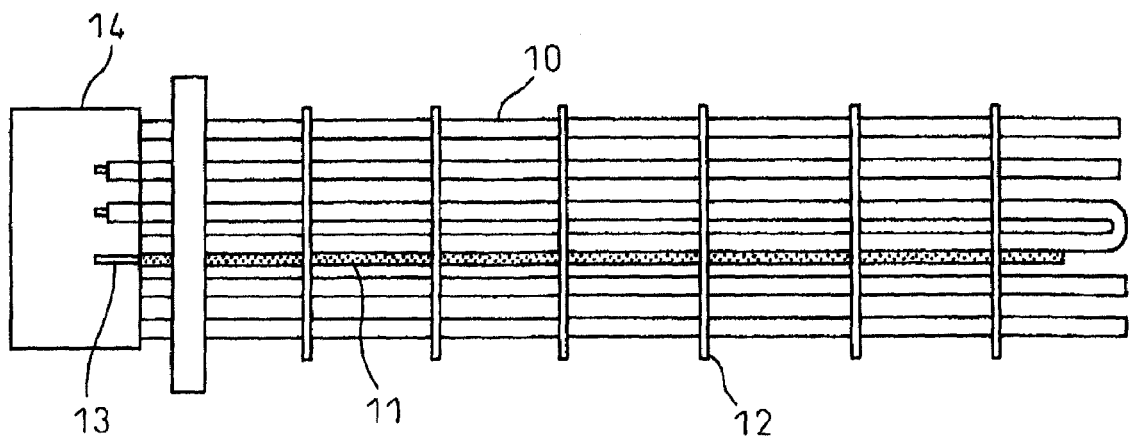
FIG. 2 is a schematic drawing showing an embodiment of a baffle-integrated heater useful for a gas treatment apparatus according to the invention.

FIG. 2 is a schematic drawing showing a detailed view of the baffle-integrated heater. The heating unit comprises a sheathed heater 10, a protecting tube 11 encasing a sheathed thermocouple 13 for temperature control, and baffles 12. The baffles 12 are mounted vertically with respect to the sheathed heater 10. Numeral 14 represents a terminal box.

Figure 3:
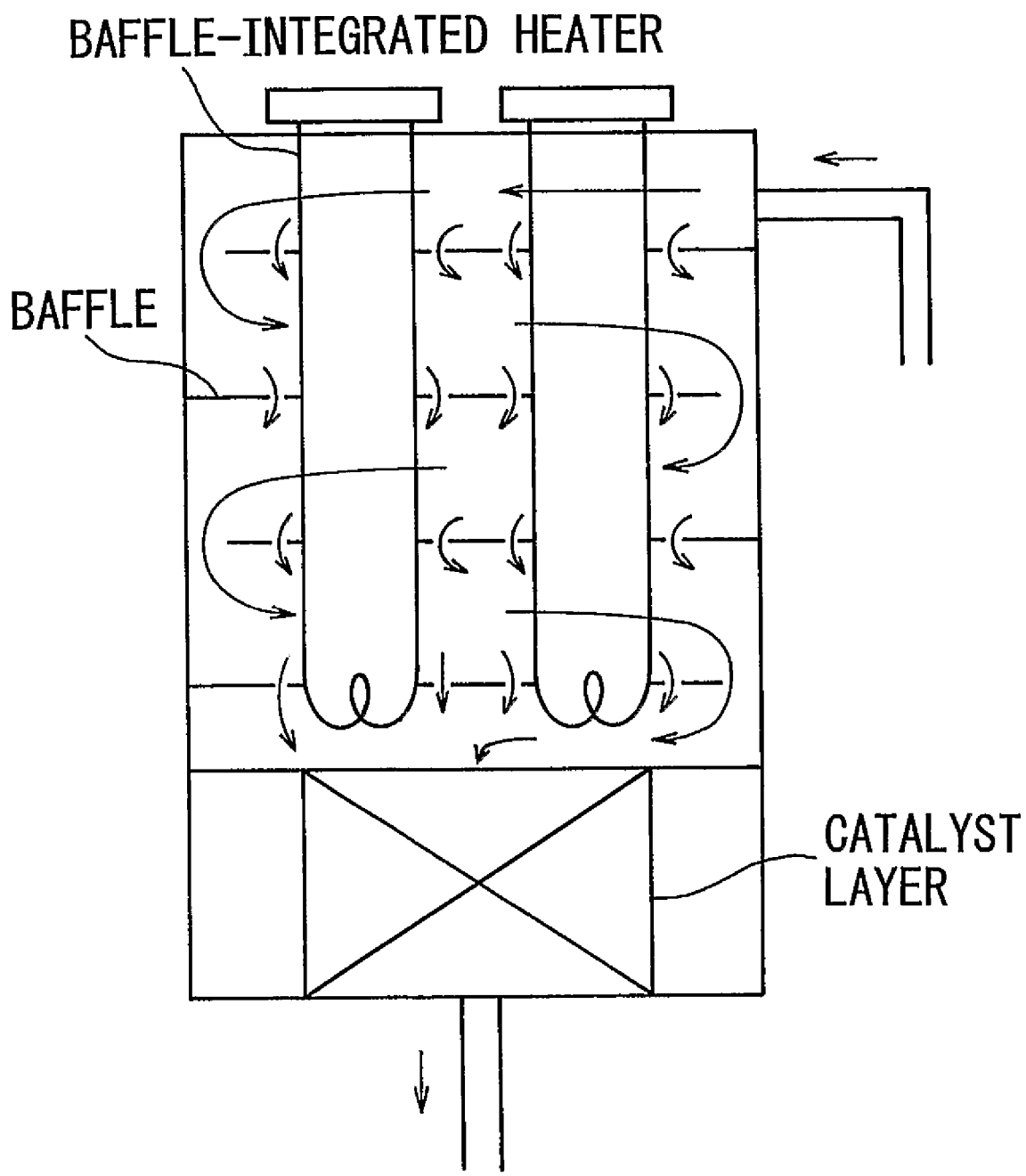
FIG. 3 is a schematic drawing showing the flow of gas in a gas treatment apparatus according to the invention.

FIG. 3 shows the flow of nitrous oxide-containing gas flowing through a treatment apparatus of the invention. Specifically, the gas introduced from the gas introduction tube shown in the drawing at the upper right of the unit into the nitrous oxide decomposition reactor enters the flow channel which includes the heating unit and a plurality of gaps, and the gas is split into a gas stream flowing along the flow channel and a gas stream flowing through the gaps formed in the flow channel, with the gas stream flowing along the flow channel being directed to merge with the split gas stream. Contact with the heating unit at this time raises the temperature to a prescribed temperature. The gas then contacts with the nitrous oxide decomposition catalyst for decomposition into nitrogen and oxygen and discharge from the gas discharge tube.

INDUSTRIAL APPLICABILITY

The present invention is of high industrial value since it allows efficient heat exchange of nitrous oxide-containing gas discharged from delivery rooms, dental clinics and the like with a heat exchanger and then decomposition of the nitrous oxide into nitrogen and oxygen, permits the global warming gas nitrous oxide to be neutralized instead of being released into the atmosphere, and further permits continuous treatment of nitrous oxide-containing gas at 1 $m^3$/min or greater.

The invention claimed is:

1. A treatment method for nitrous oxide-containing gas, wherein in a method of contacting nitrous oxide-containing gas with a catalyst for decomposition treatment of the nitrous oxide in said gas, said gas is introduced into a flow channel comprising a heating unit and multiple gaps, said gas is split into a gas stream flowing along the flow channel and a gas stream flowing through the gaps formed in the flow channel, the gas stream flowing along the flow channel is directed to merge with the split gas stream, and said gas is contacted with the heating unit to raise the temperature to a prescribed temperature before contacting with a catalyst for decomposition of the nitrous oxide.

2. A gas treatment method according to claim 1, wherein the gaps formed in said flow channel are either formed between the baffles integrally formed with the heating unit, or between the baffles integrally formed with the heating unit and the baffles formed on the walls of the decomposition reaction unit.

3. A gas treatment method according to claim 1, wherein the concentration of the nitrous oxide contained in said gas is between 10 ppm and 30%.

4. A gas treatment method according to claim 1, wherein the nitrous oxide decomposition temperature is 200-600° C.

5. A gas treatment method according to claim 1, wherein the content of $NO_x$ produced during decomposition of the nitrous oxide is no greater than 5 ppm.

6. A gas treatment method according to claim 1, wherein the concentration of nitrous oxide contained in the nitrous oxide-decomposed gas is detected and the nitrous oxide decomposition temperature is controlled based on the detected nitrous oxide concentration.

7. A treatment apparatus for nitrous oxide-containing gas, wherein a unit in which nitrous oxide-containing gas is contacted with a catalyst for decomposition treatment of the nitrous oxide in said gas comprises a heat exchanger, a heating unit integrally formed with baffles, a decomposition reactor filled with a nitrous oxide decomposition catalyst and a detector which detects the concentration of nitrous oxide in the gas exiting the decomposition reactor, wherein a gas flow channel is formed by the baffles integrally formed with said heating unit, the baffles formed on the walls of the decomposition reaction unit and the walls of the decomposition unit, while gaps are formed in said flow channel either between said baffles, or between said baffles and the baffles formed on the wall of the decomposition reaction unit.

8. A gas treatment apparatus according to claim 7, wherein the nitrous oxide-containing gas is introduced into a heat exchanger and then allowed to flow through said gas flow channel and a decomposition reactor, and discharged after being again circulated through the heat exchanger.

9. A gas treatment apparatus according to claim 7, which is provided with a temperature controlling unit which detects the concentration of nitrous oxide in the gas with said detector before and after it is introduced into the heat exchanger, and controls the temperature of said decomposition reactor based on the detected nitrous oxide concentration.

10. A gas treatment apparatus according to claim 7, wherein the heating unit integrally formed with the baffles is detachable from said decomposition treatment apparatus.

* * * * *